(12) United States Patent
Dahlin

(10) Patent No.: US 6,409,994 B1
(45) Date of Patent: Jun. 25, 2002

(54) PREPARATION FOR DENTAL TREATMENT

(75) Inventor: Stefan Dahlin, Hovas (SE)

(73) Assignee: MediTeam Dental AB, Savedalen (SE)

( * ) Notice: Subject to any disclaimer, the term of this patent is extended or adjusted under 35 U.S.C. 154(b) by 0 days.

(21) Appl. No.: 09/889,482

(22) PCT Filed: Dec. 22, 1999

(86) PCT No.: PCT/SE99/02456
§ 371 (c)(1),
(2), (4) Date: Jul. 18, 2001

(87) PCT Pub. No.: WO00/42974
PCT Pub. Date: Jul. 27, 2000

(30) Foreign Application Priority Data

Jan. 19, 1999 (SE) ............................. 9900148

(51) Int. Cl.$^7$ ............................. A61K 7/22; A61K 6/00; A61K 7/20; A61K 33/22; C11D 3/395
(52) U.S. Cl. .................... 424/53; 510/379; 510/369; 433/141
(58) Field of Search .......................... 424/53

(56) References Cited

U.S. PATENT DOCUMENTS

| | | | | |
|---|---|---|---|---|
| 3,684,722 A | * | 8/1972 | Hynam et al. ............... 252/98 |
| 3,903,252 A | * | 9/1975 | Stearns et al. .............. 424/49 |
| 3,956,158 A | * | 5/1976 | Donaldson ................. 252/102 |
| 4,271,030 A | * | 6/1981 | Brierley et al. ............... 252/98 |
| 4,585,570 A | * | 4/1986 | Nelson ...................... 252/102 |
| 5,026,523 A | * | 6/1991 | Taya ........................... 422/16 |
| 5,688,756 A | * | 11/1997 | Garabedian et al. ........ 510/369 |
| 5,697,985 A | * | 12/1997 | Good et al. ................... 8/528 |
| 5,827,810 A | * | 10/1998 | Brodbeck et al. ........... 510/369 |
| 5,851,421 A | * | 12/1998 | Choy et al. ............ 252/187.26 |
| 5,997,764 A | * | 12/1999 | Ambuter et al. ....... 252/186.25 |
| 6,017,515 A | * | 1/2000 | Van Den Bosch ............ 424/53 |
| 6,083,422 A | * | 7/2000 | Ambuter et al. ....... 252/187.26 |
| 6,099,310 A | * | 8/2000 | Bornstein et al. ........... 433/141 |
| 6,100,228 A | * | 8/2000 | Argo et al. ................. 510/379 |

FOREIGN PATENT DOCUMENTS

EP   0 398 893 B1   10/1993

* cited by examiner

*Primary Examiner*—Shep K. Rose
(74) *Attorney, Agent, or Firm*—Connolly Bove Lodge & Hutz, LLP

(57) ABSTRACT

The present invention relates to a two-component preparation for chemical-mechanical treatment of caries. The inventive preparation consists of a two-components: a first component comprising active chlorine; and a second component comprising a non-acidic amine, a gelling agent such as carboxymethylcellulose, and a dye agent, such as erythrosin, that interacts with carious material.

7 Claims, No Drawings

PREPARATION FOR DENTAL TREATMENT

The present invention relates to a preparation for chemical mechanical treatment of caries by means of a caries-dissolving two-component liquid in the form of an active, caries dissolving component and a component which reduces the reactivity and the aggressiveness of the active component to healthy tissue.

In traditional caries treatment the attacked tooth substance is removed mechanically by means of a high-speed drill. Such a caries treatment is often a painful and unpleasant experience for the patient. Some of the patients feel so uncomfortable with the treatment that they wait far too long before they go to the dentist, which means that it is often too late to, save the caries attacked teeth. Extraction of the teeth is then the only treatment method that is left.

However, there are other methods which are based on a chemical-mechanical treatment for the removal of the caries attacked tooth substance. A method of this type is described in SE 460258. According to this method a two-component liquid is mixed and then immediately applied on the caries lesion. Functioning in a biological way, the liquid makes the caries attacked substance soft without causing any damage to the tooth or the soft tissue. After 10–15 seconds the dentist can start removing the softened carious substance by scraping. The scraping procedure continues until all carious substance has been removed. Then the cavity is sealed with a suitable filling material.

Unlike the conventional mechanical caries treatment this biochemical treatment method is usually not painful at all. Neither does it require any investments in expensive equipments.

According to the treatment method the mixed two-component liquid is applied in drops on the tooth so that the entire carious lesion is covered and the caries affected tissue is softened. After 10–15 seconds a mechanical removal of the softened carious substance can be started. The softened carious dentine (the tooth substance) is removed with the use of a scraping instrument. After some scraping the solution becomes. turbid due to suspended carious substance and can be exhausted by suction or wiped away.

The above steps are repeated until the solution remains clear. In order to minimize any discomfort and pain for the patient any removal of the solution by means of a cold air stream or cold water flushing should be avoided. Instead, cotton pellets are used to remove, the solution. When the carious substance has been completely removed the cavity is sealed with a suitable filling material.

For most carious lesions the treatment has to be repeated in several steps until the solution remains clear. Due to the repetition of the procedure a relatively large volume of the two-component liquid is required. Since the liquid has a low viscosity it is easily dispersed outside the carious lesion and there is a risk for liquid waste on the surrounding tissue. It might be difficult and/or time-consuming for the dentist to remove such a solution which has been spread or which has been unintentionally spilt outside the carious lesion.

In order to facilitate the handling of such a two-component liquid it is previously known to add a viscosity increasing substance (gel substance) and a coloring agent to the liquid, see SE 96.04210-6. The gel substance should then have such properties that the aggressive influence of the sodium hypochlorite on mucous membranes is reduced, preferably it is. a carboxy methyle cellulose, and the coloring agent should have the ability to interact with the carious substance. According to a preferred embodiment the coloring agent consists of Erythrosin (E 127 B).

In addition to the fact that the gel substance and the coloring agent facilitate the application of the preparation by making it more visible and viscous, they have also other advantages in connection with the removal of carious substance. During the treatment of the carious lesion with the additional gel substance the turbidity that appears is an indication of the fact that still more carious tooth substance has to be removed. More gel substance is then applied until no more turbidity appears. This is an indication cation that all carious substance has been removed. The coloring agent has been introduced for indicating carious tooth substance, in the tooth itself before it has been removed, but also in the gel substance to make the turbidity more visible as the suspended particles in the solution are colored.

According to patent SE 460258 the two-component liquid consists of a sodium hypochlorite component and an amino acid component. The amino acid component consists of three amino acids with different charge states in the side chain. The object of the amino acids is to reduce the reactivity of the hypochlorite component, and then also the aggressivity, to healthy tissue and to direct the desired effect to proteins. This is achieved by a chlorination of the amino groups in the amino acids by the hypochlorite which is then consumed.

However, the acid itself in the amino acid compounds, i e the carboxy group which per definition belongs to each amino acid, has primarily nothing to do with the desired reactivity reducing function, other than affecting the ion activity of the solution and the pH buffering, which also can be achieved by other means. It is the amino part of the amino acid which is chlorinated, and such chlorination is the same for all amines and not just for amino acids. All chloramines then have a potential caries dissolving effect.

The advantage by using an amino acid component comprising three amino acids with different charge states according to said patent is the fact that the amino acid component then is more easily attracted to the proteins in the caries tissue, as these proteins also comprises three different charge domains. The amino acid component has in this way a "target seeking" function and the caries dissolving effect is improved. However, the carboxy group in the amino no acids has always a negative charge and is then only favourable to one of the charge states, but counteracts the other two charge states.

It is an object of this invention to provide a preparation with an improved caries dissolving effect. According to the invention the reactivity reducing component comprises one or more amines, i e compounds comprising $NH_x$, where x=1, 2 or 3 and which can be bound to one or several other chemical compounds, for instance carbon chains, and which does not contain any acid part with its negative charge, such as the carboxy group, i e an amino part without carboxy group.

So by removing the normally existing carboxy group, the caries-dissolving effect is improved for a preparation comprising three amino acids with different charge states, such as the caries-dissolving preparation Carisolv marketed by MediTeam AB.

The active component could be sodium hypochlorite or any other chloride compound with active chlorine, i e chlorine with a charge state of +1, Cl(+1).

In the following an example of a caries dissolving two component solution according to the invention will be described more in detail, in which the reactivity reducing component has been denoted by a and the active component by B.

As illustrated in the example the reactivity reducing component A in the example comprises three amines:

amino-ethan-diol, 1-amino-3,3-dimethyl-propanol and 1,5-diamino-pentanol.

| A. A solution (red) in clean (de-ionized) water consisting of: | | |
|---|---|---|
| Amino-ethane-diole | $C_2O_2NH_7$ | 34 mM |
| 1-amino-3,3-dimethylepropanol | $C_5ONH_{13}$ | 38 mM |
| 1,5-diaminopentanol | $C_5ON_2H_{14}$ | 34 mM |
| Erythrosin (E 127 B) | $Na_2C_{20}O_5T_4H_6$ | 0.04% (4.5 mM) |
| Sodium chloride | NaCl | 0.1 M |
| Sodium hydroxide | NaOH | to pH = 11 |
| Carboxy methyl cellulose (CMC) | 200–800 mPas | 3% |
| B. A solution (clear) in clean (de-ionized) water consisting of: | | |
| Potassium hypochlorite | KOCl | 0.5% (0.1 M) |

What is claimed is:

1. A preparation for chemical-mechanical treatment of caries, said preparation comprising:

a first solution, free of amines and containing active chlorine; and a second solution, free of active chlorine and containing at least one amine capable of forming a chloramine compound in the presence of active chlorine, wherein said at least one amine is free of carboxyl groups, said amine having at least one proton bound to at least one amino-nitrogen.

2. A preparation according to claim 1, wherein said at least one amine comprises carbon.

3. A preparation according to claim 2, wherein said at least one amine is selected from the group consisting of aminoethandiol, 1-amino-3,3-dimethyl-propanol and 1,5-diaminopentanol.

4. A preparation according to claim 1, wherein said active chlorine comprises hypochlorite.

5. A preparation according to claim 1, wherein said second solution comprises a gelling agent.

6. A preparation, according to claim 5, wherein said gelling agent is carboxymethylcellulose.

7. A preparation, according to claim 1, wherein said active chlorine comprises chlorine in a $1^+$ oxidation state.

* * * * *